United States Patent [19]
Park et al.

[11] Patent Number: 6,019,880
[45] Date of Patent: Feb. 1, 2000

[54] HGO-MODIFIED ELECTRODE FOR ANODIC STRIPPING ANALYSIS

[75] Inventors: Jongman Park, 102-1403 Kukje-Sanjang Apartment, 1693, Sillim-10-Dong, Kwanak-Ku, Seoul; Kyoungwon Seo; Jung-Yeun Choi, both of Seoul, all of Rep. of Korea

[73] Assignee: Jongman Park, Seoul, Rep. of Korea

[21] Appl. No.: 09/098,380

[22] Filed: Jun. 17, 1998

[30] Foreign Application Priority Data

Jun. 19, 1997 [KR] Rep. of Korea ............. 97-25939
Jun. 3, 1998 [KR] Rep. of Korea ............. 98-20666

[51] Int. Cl.$^7$ ................................. G01N 27/26
[52] U.S. Cl. ............... 204/413; 204/434; 204/290 R; 204/291; 204/294
[58] Field of Search ................. 204/413, 434, 204/294, 290 R, 291

[56] References Cited

U.S. PATENT DOCUMENTS

| | | | |
|---|---|---|---|
| 3,859,193 | 1/1975 | Bednarski et al. | 204/413 |
| 3,914,509 | 10/1975 | Tennemt | 204/413 |
| 4,933,062 | 6/1990 | Shaw et al. | 204/294 |
| 4,957,593 | 9/1990 | Shaw et al. | 204/291 |
| 5,002,651 | 3/1991 | Shaw et al. | 204/290 R |
| 5,429,725 | 7/1995 | Thorpe et al. | 204/291 |
| 5,739,039 | 4/1998 | Girult et al. | 204/413 |

*Primary Examiner*—Bruce F. Bell
*Attorney, Agent, or Firm*—Browdy and Neimark

[57] ABSTRACT

Two types of HgO-modified electrodes are disclosed. The HgO-modified electrode according to the present invention comprises, HgO particles as precursor of mercury, which can be exposed on the surface of the said electrode and then can be reduced electrochemically into micro-droplets of mercury; and electro-conductive material to maintain optimal conductivity of the said modified electrode. In the HgO-modified electrode according to the present invention, built-in mercury precursor, HgO can be utilized feasibly for the generation of the surface mercury droplets by in situ electrochemical treatment or pretreatment without necessity of $Hg^{2+}$ solution. The electrode surface can be renewed easily either by a simple polishing process for the bulk-modified electrode type-I or by simple exchange for the screen-printed disposable type modified electrode type-II. So further simplification of anodic stripping analysis process is possible by employing the HgO-modified electrodes according to the present invention.

9 Claims, 7 Drawing Sheets

HGO-MODIFIED ELECTRODE FOR ANODIC STRIPPING ANALYSIS

BACKGROUND OF THE INVENTION

1. Field of the Invention

The present invention relates to a modified electrode for anodic stripping analysis. Particularly, it is relates to a modified electrode which containing mercury oxide as built-in mercury precursor.

2. Discussion of Related Art

Anodic stripping analysis has been known as one of the most sensitive techniques and widely used for trace heavy metal analysis in various samples because of its capability of preconcentration of analytes on the surface of the electrode.

In general, mercury electrodes such as the hanging mercury drop electrode (HMDE) or thin-film mercury electrode (TFME) have been used for anodic stripping analysis because of their distinctive analytical characteristics. However, use of the hanging mercury drop electrode has been hesitated due to the difficulties in handling liquid mercury and disposing of used mercury. Hence, use of the thin-film mercury electrode is preferred because of its improved convenience and sensitivity. If the thin-film mercury electrode used along with fast scan stripping voltammetric techniques, cumbersome deoxygenation step can be skipped. Although the improved sensitivity and analytical convenience of the thin-film mercury electrode may still attract analysts to choose the stripping analysis technique for trace heavy metal analysis in laboratories or in the field, a film generation step either from a solution of $Hg^{2+}$ or in situ by addition of $Hg^{2+}$ to sample solutions should be always involved. A drawback of the thin-film mercury electrode is instability of mercury thin-film formed at the surface of glassy carbon electrodes, which affects the reproducibility of analysis. Although there have been extensive studies on the improvement of the stability of mercury film, it is not satisfactory yet.

General modified composite electrodes are disclosed in U.S. Pat. No. 4,957,593 and U.S. Pat. No. 5,002,651.

According to the U.S. Pat. No. 4,957,593, the modifiers of the disclosed modified composite electrodes may provide the characteristics of electroactivity, inclusion, adsorption or electrocatalysis to the surface of the electrode in a solution. Also, after use, the electrode surface may be renewed by removing the surface portion deactivated and thereby exposing a fresh portion of the uniform electrode matrix.

According to the U.S. Pat. No. 5,002,651, the renewable composite microelectrodes for electrochemical applications are formed by an initial coating on an elongated conductive substrate of less than 500 micrometers over at least a portion of its length with a modifier composition, and superposed coating of electronically resistive polymer. The microelectrode will normally be used with only the tip portion thereof immersed in the solution, and it may be renewed by removing the contaminated tip portion.

SUMMARY OF THE INVENTION

According to the present invention, the HgO-modified electrodes are provided by adapting composite electrode technique. They are compatible to the thin-film mercury electrode in the anodic stripping analysis of heavy metals. The HgO-modified electrodes according to the present invention comprises, HgO particles as built-in precursor of mercury, which can be exposed on the surface of the said electrodes and then can be reduced electrochemically into microdroplets of mercury.

The first type of the HgO-modified electrode according to the present invention is a bulk-modified electrode (type-I), which contains highly dispersed HgO particles as precursors of mercury through the whole electrode matrix. Fine particles of HgO exposed on the surface of the electrode can be reduced electrochemically into microdroplets of mercury, which are adhered on the surface of the electrode and relatively stable during electrochemical analysis. The surface of the bulk-modified electrode can be renewed easily by a simple polishing process.

The second type of the HgO-modified electrode according to the present invention is a screen-printed disposable type electrode (type-II) which contains HgO-modified electrode layer at the tip of an inactive substrate. The fine particles of HgO in the modified electrode layer is exposed to the solution and can be reduced electrochemically into the microdroplets of mercury. The type-II electrode layer according to the present invention can be fabricated into a disposable type sensor by forming a reference electrode such as Ag/AgCl, and a counter electrode together on the same substrate.

In the applications of both types of the HgO-modified electrodes according to the present invention, no more $Hg^{2+}$ solution is required for the generation of the mercury thin-film. The electrode surface can be renewed easily either by a simple polishing process for the bulk-modified electrode or by simple exchange for the disposable type sensing probe. Hence, further simplification of anodic stripping analysis process is possible by employing the HgO-modified electrodes according to the present invention.

It is to be understood that both the foregoing general description and the following detailed description are exemplary and explanatory, and are intended to provide further explanation of the invention as claimed.

BRIEF DESCRIPTION OF THE ATTACHED DRAWINGS

The accompanying drawings, which are included to provide further understanding of the invention and are incorporated in and constitute a part of this specification, illustrate embodiments of the invention and serve to explain the principles of the present invention along with the description.

In the drawings:

FIGS. 1a and 1b shows the surface morphology of the HgO-modified electrode (type-I) containing 16.7 weight % of HgO according to the present invention, FIG. 1a shows the polished surface before electrochemical conditioning. FIG. 1b shows the surface after conditioning at −0.4 V vs. Ag/AgCl, 0.01 M KCl and 0.01 M HCl for 100 sec;

Figure 4:
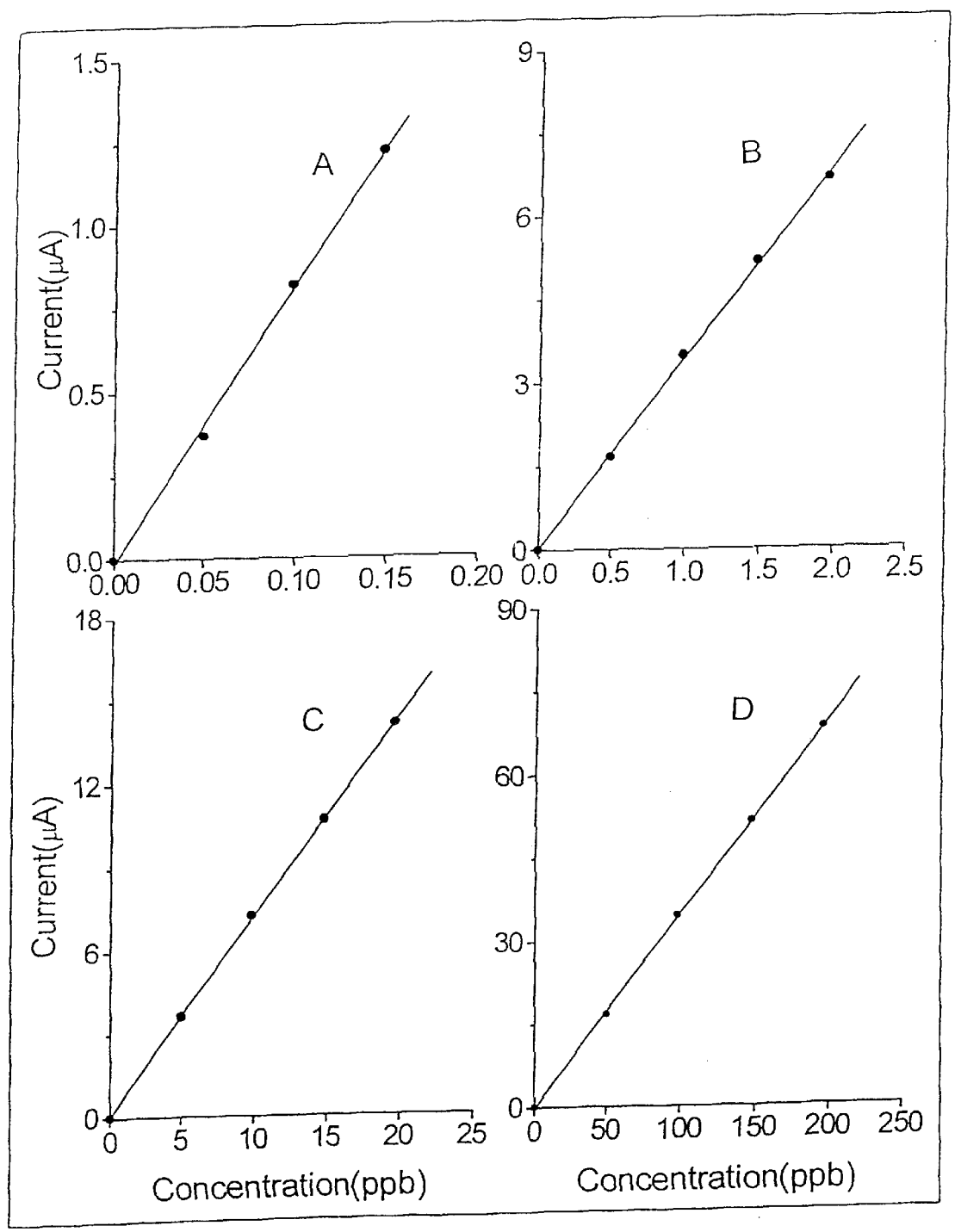
Figure 5:
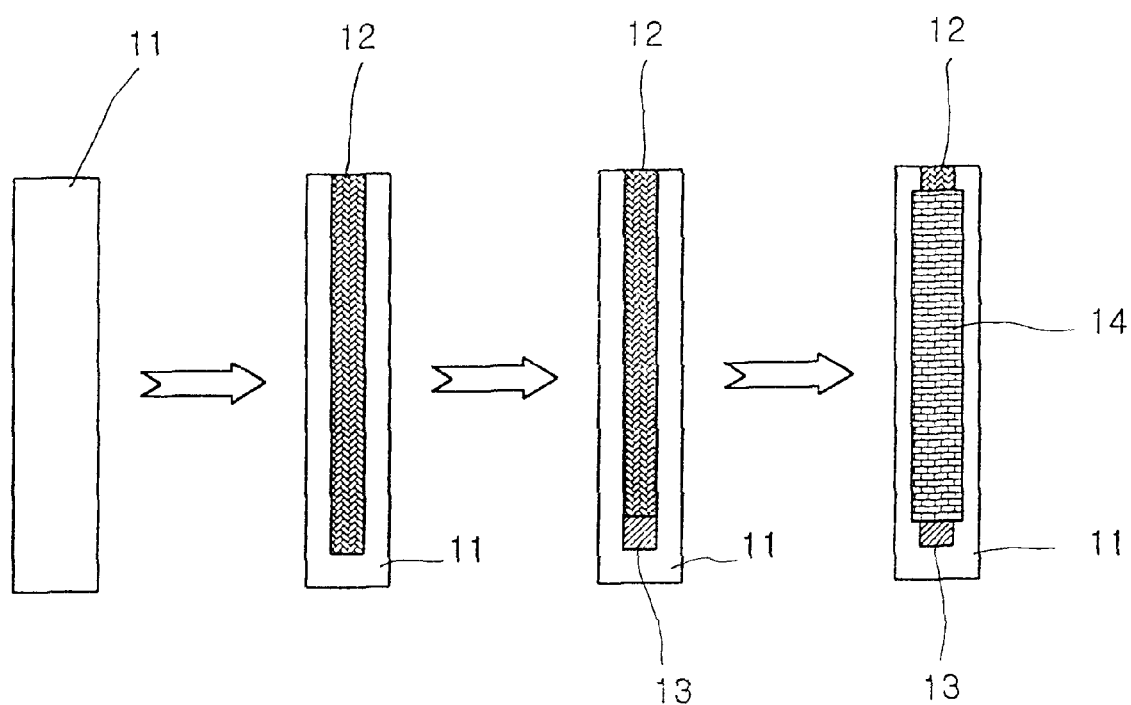
Figure 6:
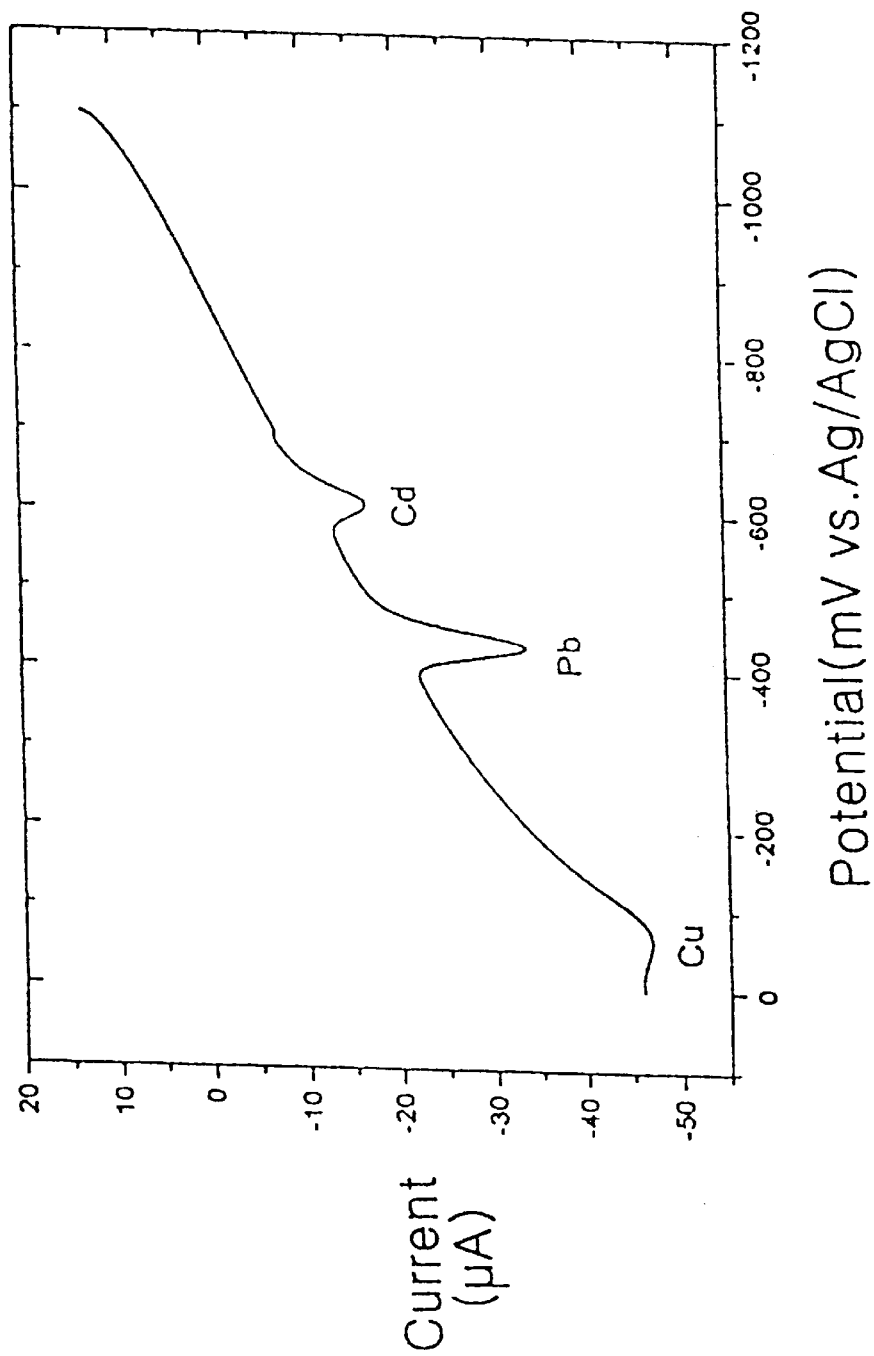
Figure 7:
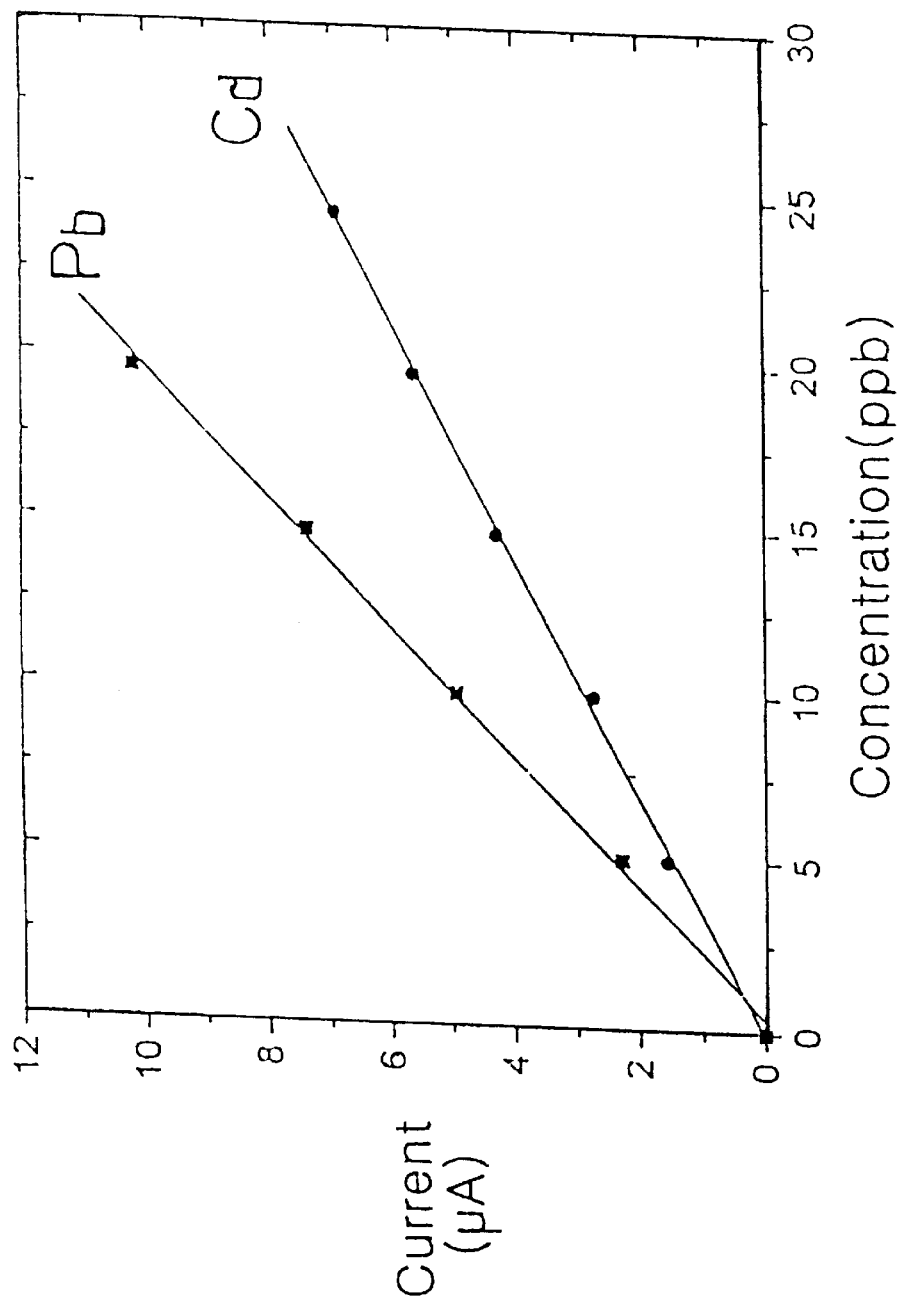

FIG. 4 is linear calibration curves for various ranges of Pb concentration obtained with the HgO-modified electrode (type-I) containing 16.7 weight % of HgO according to the present invention. Deposition time: A for 15 min., B for 4 min., C for 1 min., D for 20 sec.;

FIG. 5 shows the preparation process of the HgO modified electrode (type-II) according to the present invention;

FIG. 6 is an anodic stripping voltammogram of Cu, Pb, and Cd obtained with the type-II electrode containing 18.8 weight % of HgO, where concentration of each metal is 10 ppb in 0.1 M KCl and 0.01 M HCl solution;

FIG. 7 is linear calibration curves for various ranges of Pb and Cd concentration obtained with the type-II electrode containing 18.8 weight % of HgO;

FIG. 8 shows the fabrication process of a sensor probe by integrating the type-II HgO-modified electrode, a reference electrode (Ag/AgCl) and a counter electrode on a single substrate.

DETAILED DESCRIPTION OF PREFERRED EMBODIMENT

Reference will now be made in detail to the preferred embodiments of the present invention, examples of which are illustrated in the accompanying drawings.

The following example 1 relates to both HgO-modified electrodes, type-I and type-II.

EXAMPLE 1

Preparation of the mixture of carbon black and HgO particles for the type-I and type-II electrodes The following is a typical procedure for the preparation of the mixture of carbon black and HgO particles, which can be used for the preparation of the type-I and type-II HgO-modified electrodes of the present invention.

Mercuric chloride 8.35 g is dissolved in 200 ml of ethanol. Two grams of carbon black is added to this solution and the mixture is sonicated to disperse the carbon black thoroughly. The relative amount of mercuric chloride to carbon black can be changed to control the content of mercuric oxide in the electrode matrix. Deionized water is added slowly with vigorous stirring until the content of ethanol become 20 to 30%. Ethanol is used to disperse the agglomerated hydrophobic carbon black well into fine particles.

The mixture is titrated with 1.5 M NaOH solution to precipitate $Hg^{2+}$ into HgO. It should be noted that the precipitation process is an important step affecting the performance of modified electrodes. Precipitated mercuric oxide should be adsorbed well on the surface of dispersed carbon black so that the color of the mixture become black without any yellowish color of mercuric oxide precipitates. When the yellowish color of mercuric oxide is observed, the precipitates should be dissolved back by adding some acid solution and then reprecipitated. The mixture is filtered, washed with deionized water thoroughly, and then dried at 60 to 70° C. It is ground well into fine powder using commercial coffee bean grinder, then stored in a sealed container.

The following example 2 through 8 relate to type-I HgO-modified electrode.

EXAMPLE 2

Preparation of the type-I HgO-modified electrode

The powder mixture of carbon black and HgO particles is incorporated into a polymeric matrix as follows; a solution of styrene, and divinylbenzene (4:1 ratio) containing AIBN (2,2'-azobidisobutyronitrile) as radical initiator is added slowly to the mixture of carbon black and mercuric oxide until a thick paste formed. The content of carbon black is controlled at 5.2 weight % in order to ensure proper electrical conductivity of the resulting composite materials while the mercuric oxide content is varied to get electrodes containing different amounts of modifier.

The amount of AIBN is kept to about 1 weight % of the mixture. The paste is polymerized in sealed glass tubing at 70° C. for more than 4 hours. The resulting HgO-modified composite materials are fabricated into proper types of electrodes by either sealing in glass tubing with commercial epoxy resin for ordinary stripping analysis or press-fit into Teflon body for rotating disk electrode experiments. The electrodes are ground with SiC abrasive paper, then finally polished with 0.05 µm alumina. The electrodes are washed thoroughly with deionized water between each step.

The HgO-modified electrode, type-I obtained in example 1 reveals the proper physical and chemical properties for fabrication. The polished surface is smooth and shiny. Since fresh HgO modifier particles are exposed on the surface upon polishing, they can be reduced electrochemically to fine droplets of mercury during the conditioning process or deposition process of analytes.

EXAMPLE 3

Surface morphology of the HgO-modified electrode type-I

Figure 1A:
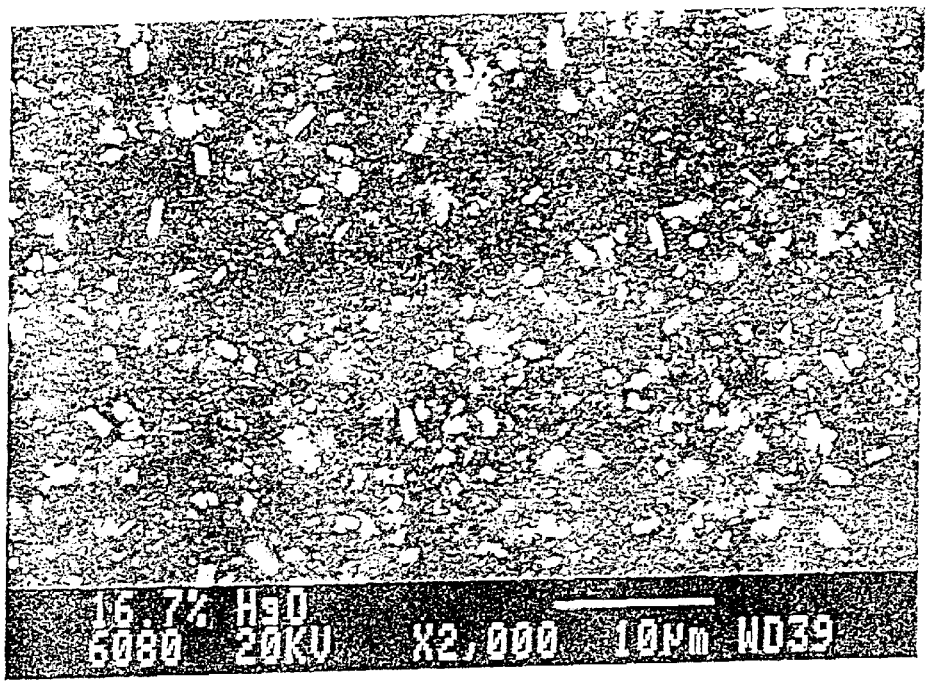

The surface morphology of an electrode containing 16.7% HgO is shown in FIG. 1.

Micro-crystalline mercury oxide particles (white and blurry white spots) are distributed randomly along with carbon black agglomerates (gray) in the polymeric matrix (background). The mercuric oxide particles are not uniform in size, but it did not exceed 3 µm.

Figure 1B:
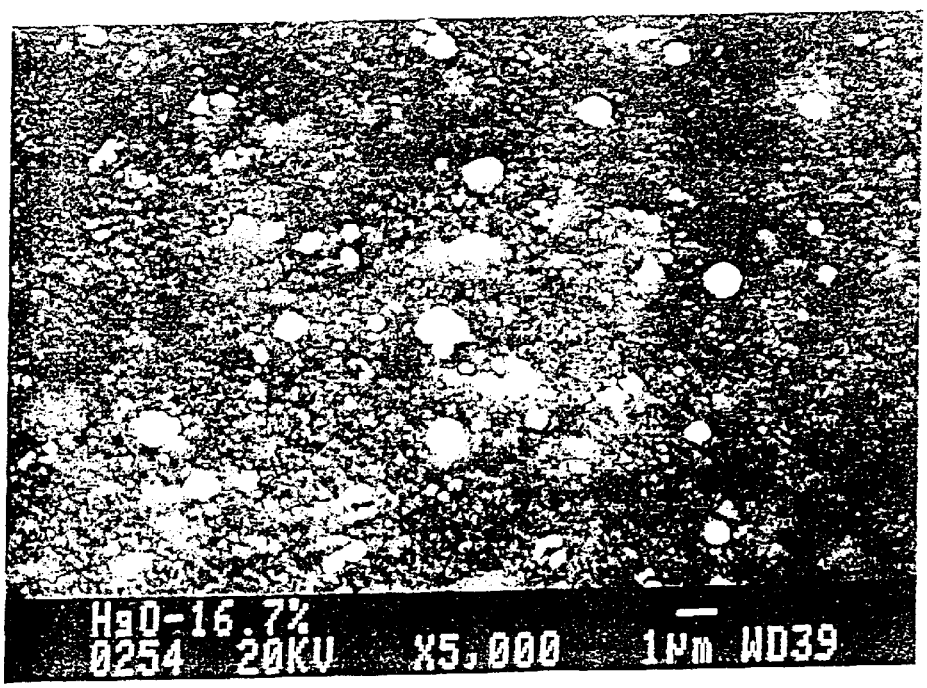

FIG. 1b shows the surface morphology after electrochemical conditioning at −0.40 V vs. Ag/AgCl for 100 sec. Mercury droplets are randomly distributed over the surface. They are mostly smaller than 1.5 µm. Most mercury droplets filled and stuck in hollow spots with large wetting angles. Some others are partially exposed on the surface because the precursor particles are partially buried in the electrode matrix.

However, it should be recognized that the sizes of mercury droplets pictured must be somewhat smaller than those initially conditioned because of the instability of mercury droplets under the high vacuum of a scanning electron microscope (SEM). During the observation of the surface morphology through CRT screen gradual disappearance of small mercury droplets is noted. The blurry white spots are though to be HgO precursors buried completely in the electrode matrix, which can not be reduced to mercury droplets.

It is thought that large surface interaction between the electrode matrix and fine mercury droplets plays an important role for stabilizing the mercury droplets on the electrode surface. Large agglomerated of mercury oxide particles are observed in some batches containing a large amount of modifier, which become large droplets of mercury by conditioning. Large droplets would be fallen easily from the surface even with weak disturbance. Eventually the stripping analysis signals are affected by the presence of large mercury droplets. Often the first stripping signals obtained just after electrode conditioning process are somewhat larger than others when the electrodes are rotated during the deposition steps. So the precipitation process of HgO should be carefully controlled to avoid formation of large HgO agglomerates. However, satisfactory results could be obtained if any yellowish color of mercuric oxide is not observed during the precipitation process.

The mercuric oxide content in the electrode matrix is an important factor affecting on the analytical characteristic of the electrodes. Hydrogen evolution overpotential, stability and reproducibility of the electrode are dependent on the surface concentration of reduced mercury.

The surface concentrations of the mercury can be estimated from the charges required to oxidize Hg(0) to Hg(II). Anodic peaks ($E_\Sigma$=+0.75 V vs. Ag/AgCl) of linear sweep voltammograms are integrated to get the charges after conditioning at −1.0 V for 120 sec. In most case the surface concentration of mercury increased linearly with slop n≅2 as the mercuric oxide content increased. The amount of mercuric oxide exposed on the surface might increase drastically because of not only the increment of mercuric oxide but also the decrease of polymeric content.

Typically the estimated surface mercury concentration of the electrode containing 16.7% HgO is $1.3 \times 10^{-8}$ mol/cm$^2$, which is about the same order of magnitude to those of ordinary thin-film mercury electrodes. The surface concentrations of the mercury are not altered apparently although the electrodes are sonicated for 1 minute before conditioning. The mercuric oxide particles must be held strongly on the surface by the polymeric matrix.

EXAMPLE 4

Anodic stripping voltammetry using the HgO-modified electrode type-I

Figure 2:
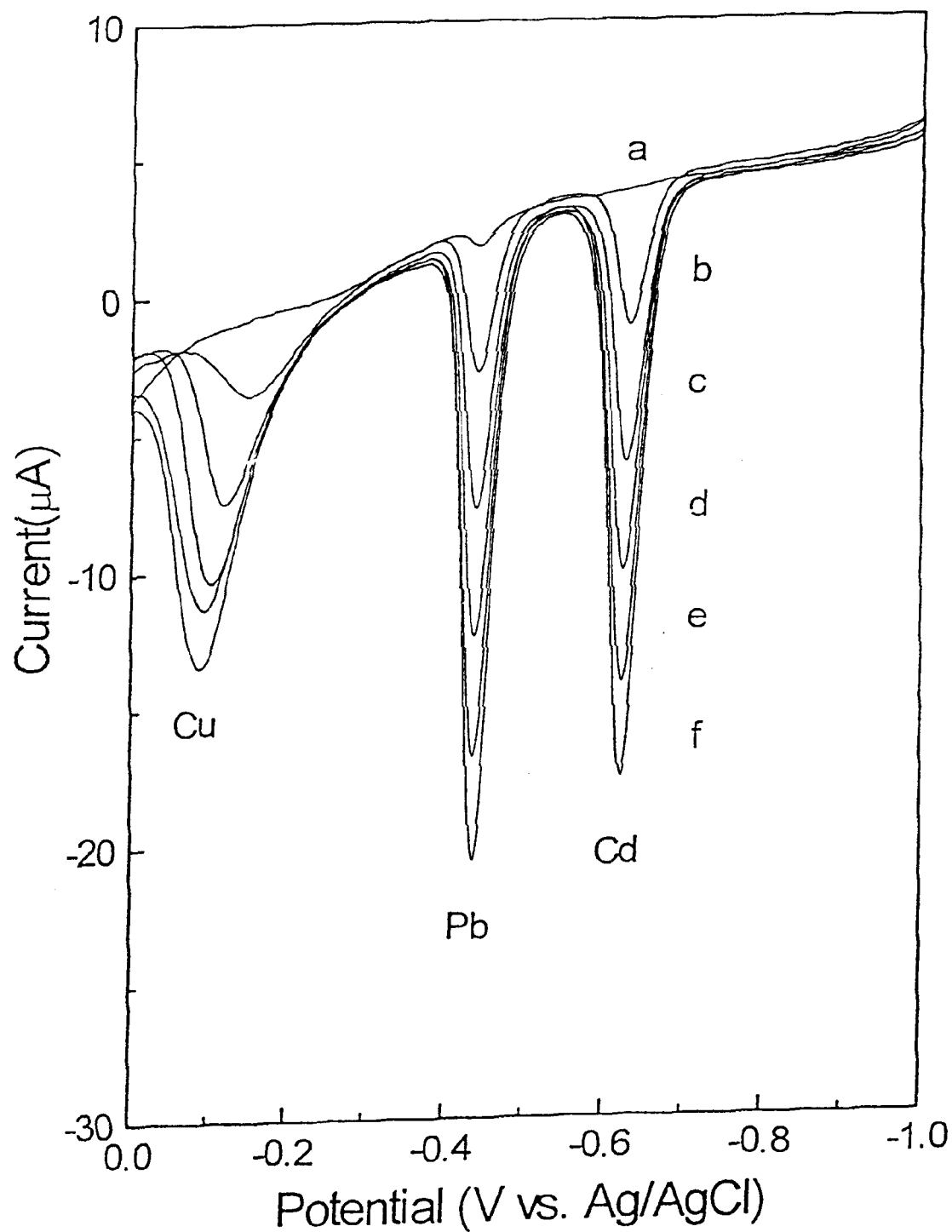
FIG. 2 is anodic stripping voltammograms for Cu, Pb, and Cd obtained with the HgO-modified electrode (type-I) containing 16.7 weight % of HgO according to the present invention, (a) background, (b) 5 ppb of each metal ion, (c) 10 ppb, (d) 15 ppb, (2) 20 ppb in 0.1 M KCl and 0.01 M HCl solution.

Fast-scan anodic stripping voltammetry is performed for Cu, Pb, and Cd using electrode containing 16.7 weight % HgO to demonstrate the possibility of its utilization and shown in FIG. 2. The electrode is conditioned ar −0.4 V for 400 sec. in 0.1 M KCl, 0.01 M HCl solution to form mercury droplets, and then cleaned at 0.0 V for 20 sec. Metals are deposited at −1.0 V for 60 sec, equilibrated for 10 sec, and then stripped at 2.0 V/sec. The solution is stirred with a magnetic stirrer at constant rate during the conditioning, cleaning, and deposition steps. Between the measurements the electrode is cleaned at 0.0 V for 20 sec. The deoxygenation step is skipped by employing the fast scan stripping technique as mention earlier. The stripping peak currents for Pb and Cd increase linearly with the concentration increase. Meanwhile, the linearity for Cu is inferior to those of others because of severe band broadening owing to the complicated oxidation process of copper.

EXAMPLE 5

Stability of the surface mercury droplets of the HgO-modified electrode type-I

Figure 3:
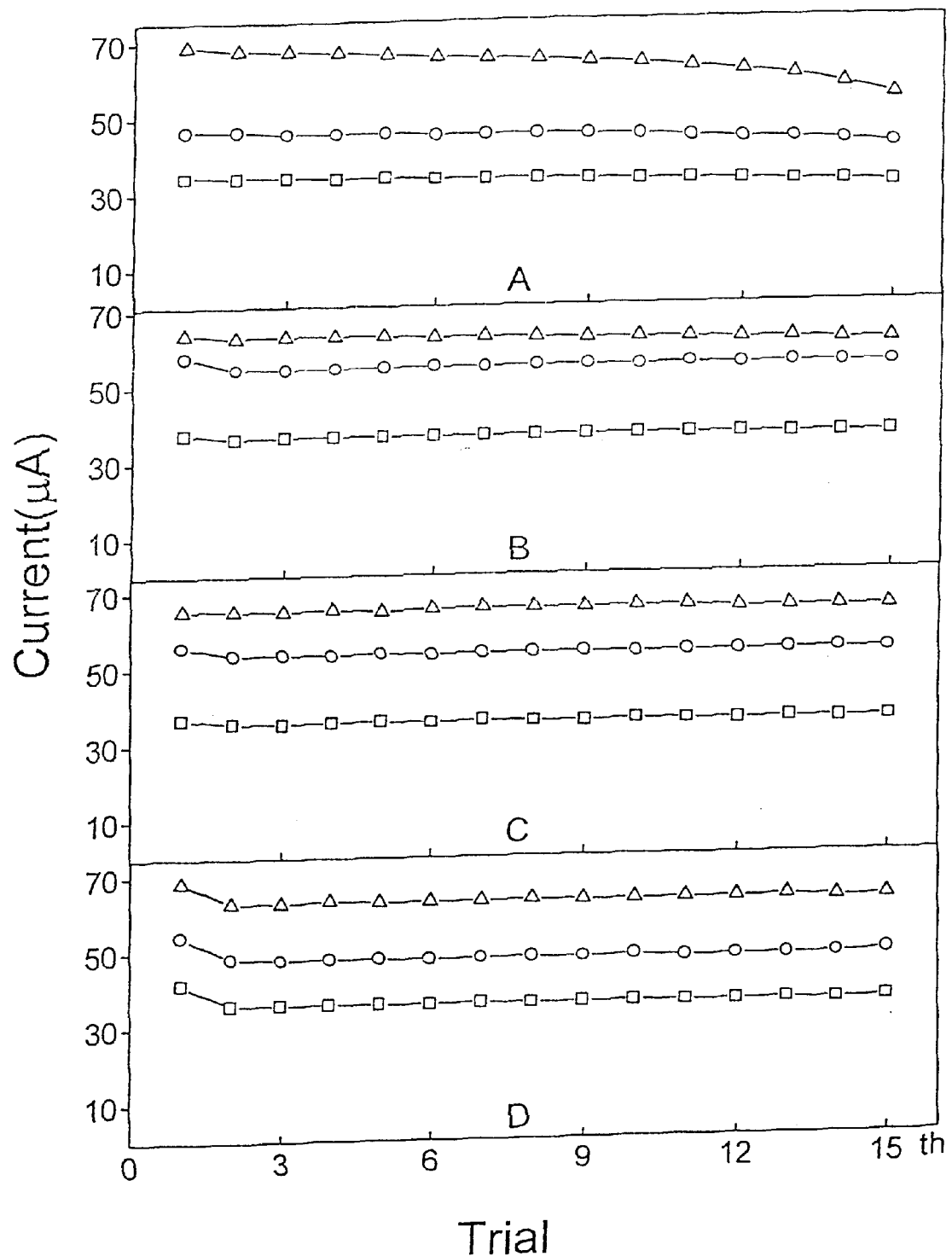
FIG. 3 shows the effects of the spin rate of type-I electrodes on the stability of the surface mercury droplets represented by anodic stripping current change, (a) HgO 6.7%, (b) HgO 10.0%, (c) HgO 13.4%, (d) HgO 16.7%, where Pb concentration is 50 ppb, □ for 500 rpm, o for 1000 rpm, Δ for 2000 rpm.

Stripping analysis is performed while the electrodes are rotated using a rotator at controlled rates, i.e., 500 rpm, 1000 rpm and 2000 rpm, to test the physical stability of the mercury droplets formed on the surface of electrodes, and the results are shown in FIG. 3.

In most measurements, the anodic stripping peak currents do not change apparently, which means the surface mercury droplets are stable enough to endure the centrifugal force exerted by electrode spinning.

However, it is not true for the electrode containing the lowest amount of HgO (6.7 weight %). Gradual decrease of the stripping current is observed which is dependent on the spin rate. If it is assumed that the centrifugal force is the major factor affecting the stability of the surface mercury droplets, the electrode containing the highest amount of HgO should be most unstable. It is thought that there must be other factors affecting the stability of the surface mercury droplets rather than the centrifugal force.

Since the major difference in the electrodes is the content of modifier affecting the hydrogen overpotential of the electrode, the active hydrogen gas evolution process would be responsible for the instability of the surface mercury droplets of the electrodes containing lower amount of HgO. The hydrogen reduction overpotentials of the electrodes containing higher amounts of HgO are negative enough to keep the droplets stable.

The remarkable stability of the surface mercury droplets would be a result of the extraordinary surface morphology of the electrodes. As mentioned earlier, the mercury droplets are filled and stuck in small hollow spots with large contact angles so that large surface interaction between the electrode matrix and mercury droplets would improve the stability. So electrodes containing a higher amount of mercury oxide in the electrode matrix are preferred.

In addition, it should be remarked that the first stripping anodic peak currents are somewhat higher apparently than others in most cases. Such differences are likely due to the instability of large-sized droplets that might fall off easily at the initial stage of the experiments. Since it appears to be reproducible, the first stripping analysis data may be rejected for reliable analytical results.

EXAMPLE 6

Linear calibration curves for various ranges of Pb concentration

The feasibility of sensitivity control of analysis by changing the deposition time is one of the advantages of the stripping analysis. In this example, the proportionality of stripping peak current versus concentration of Pb$^{2+}$ ion for several orders of concentration ranges is examined and shown in FIG. 4.

The correlation coefficients of the calibration curves appear to be higher than 0.999. When an electrode simply ground with 2,000 grit SiC paper is used, the linearity of the calibration curves is still high. Typically the correlation coefficient is 0.998 for the range of 0 to 15 ppb of Pb$^{2+}$.

Since fairly reliable results can be obtained without a polishing process, the electrodes can be utilized for on-site field analysis of heavy metals with the advantage of convenience.

In the repetitive stripping analysis of a 50 ppb Pb$^{2+}$ solution for the evaluation of the reproducibility of the anodic stripping peak current, the relative standard deviations of the responses ranges from 0.5 to 2.0% maximum. In the analysis of lead in laboratory tap water by standard addition method, the relative standard deviation of the analytical results appear to be 1.6% in 95% confidence level for seven repetitive trials, which means the analysis are highly reproducible. Between the measurements the electrode surface is polished every time.

The following example 7 through 10 relate to the type-II HgO-modified electrode.

EXAMPLE 7

Preparation of the HgO-modified electrode type-II

FIG. 5 shows the preparation process of the screen-printed disposable type HgO-modified electrode according to the present invention.

For the preparation of the screen-printed electrode the screen printable modifier ink can be formulated as follow; A portion of the mixture of carbon black and mercury oxide particles prepared according to the example 1 is added to a solution of adhesive binders, and then mixed thoroughly using a homogenizer. The adhesive binder solutions may comprises binders, such as epoxy resin, phenolic resin or PVC resin, etc., dissolved in solvents such as alcohols, THF, butyl carbitol, isophorone, etc. The net content of the carbon black in the dried modifier ink mixture should be 3 to 13 weight % to maintain proper electrical conductivity of the printed electrodes.

Any insulating substrate strip made of ceramics, epoxy resin, PVC, or polycarbonate can be used if the modifier ink reveals proper adhesion property on the substrates.

The electrochemically inactive conducting layer (layer 12 in FIG. 5) is formed on the substrate strip 11 by a screen-printing technique. The inactive conducting layer 12 is formed using any commerical screen-printing ink containing conducting carbon, silver, gold or platinum powder for electrical circuit board preparations.

On the one end of the inactive conducting layer 12, the modifier ink containing HgO is screen-printed to form the HgO-modified electrode layer 13. The thickness of the modified electrode layer 13 is about 10 to 100 $\mu$m. Finally, the insulating dielectric masking layer 14 is formed over the conducting layers as shown in FIG. 5 except the both end of the electrode. The exposed inactive conducting layer serves for electrical contact while the exposed modifier layer on the other end does for electrochemical sensing. The printed layers should be dried and cured properly just after each printing step.

EXAMPLE 8

Anodic stripping voltammogram of Cu, Pb, and Cd obtained with the HgO-modified electrode type-II Fast-scan anodic stripping voltammetry is performed for Cu, Pb, and Cd using the electrode prepared by the fabrication process of the example 7, and the result is shown in FIG. 6. The screen-printed HgO-modified electrode contains 18.8 weight % HgO. The electrode is conditioned at −0.7 V for 5 min. in 0.1 M KCl, 0.01 M HCl solution to form the surface mercury droplets, and then cleaned at −0.10 V for 10 sec. Metals are deposited at −1.1 V for 2 min., and then stripped linearly at 4.0 V/sec. As shown in FIG. 6, each stripping peak current for Cd, Pb, and Cu appears at −0.61 V, −0.43 V and −0.07 V respectively.

EXAMPLE 9

Linear calibration curves for Pb and Cd

FIG. 7 shows the standard calibration curves for various ranges of Pb and Cd concentration obtained with the 18.8 weight % HgO-modified electrode type-II.

The standard calibration curves appear to be linear in the concentration ranges of 0 to 25 ppb for Pb and Cd. The correlation coefficient of the calibration curves are higher than 0.998. It is also possible to analyze Pb and Cd in a solution simultaneously.

EXAMPLE 10

Preparation of the disposable sensor probe for anodic stripping analysis

FIG. 8 shows the fabrication process of the screen-printed disposable sensing probe by integrating the HgO-modified electrode, Ag/AgCl reference electrode, and counter electrode on a single substrate.

Three separate inactive conducting layers 22 are formed on the insulating substrate 21. Two separate conducting carbon layers 23 are formed on the one end of the both outside inactive conducting layer 22. Then, Ag/AgCl reference electrode layer 24 is formed on the same end of the remaining inactive conducting layer 22 at the center of the substrate.

On the one of the said two carbon layers 23, the HgO-modifier ink obtained in the said example 7 is coated to form a modified electrode layer 25. Finally, the insulating dielectric masking layer 26 is formed over the conducting layers as shown in FIG. 8 except the both end of the sensor. The exposed inactive conducting layers 22 serve for electrical contact while the exposed modifier layer 25, Ag/AgCl reference electrode layer 24, and carbon counter electrode layer 23 on the other end serve together for electrochemical sensing. The printed layers should be dried and cured properly just after each printing step.

It will be apparent to those skilled in the art that various modifications and variations can be made in the HgO-modified electrode of the present invention without deviating from the spirit or scope of the invention. Thus, it is intended that the present invention cover modifications and variations of this invention provided they come within the scope of the appended claims and their equivalents.

What is claimed is:

1. HgO-modified electrode for anodic stripping analysis, the electrode comprising:

HgO particles as precursor of mercury, which can be exposed on the surface of the said electrode and then can be reduced electrochemically into micro-droplets of mercury; and electro-conductive material to maintain proper electrical conductivity of the said modified electrode.

2. The modified electrode according to claim 1, wherein the said HgO particles and the said electro-conductive material are dispersed through whole electrode matrix which is prepared from polymers.

3. The modified electrode according to claim 2, wherein the said HgO particles is amount of about 1–40 percent by weight of the electrode whole matrix.

4. The modified electrode according to claim 2, wherein a tip of the electrode is renewed by grinding.

5. The modified electrode according to claim 1, wherein the mixture of said HgO particles and the said electro-conductive material is coated on the insulating substrate.

6. The modified electrode according to claim 5, wherein the said HgO particles is amount of about 1–40 percent by weight of the said mixture.

7. An apparatus for anodic stripping analysis comprising a single insulating substrate on which is formed the modified electrode according to claim 5, a Ag/AgCl reference electrode, and counter electrode.

8. The modified electrode according to claim 1, wherein the said electro-conductive material is carbon black.

9. The modified electrode according to claim 1, wherein the HgO particles are obtained by precipitation of $Hg^{2+}$ ion.

* * * * *